US008529626B2

(12) United States Patent
Seme

(10) Patent No.: US 8,529,626 B2
(45) Date of Patent: Sep. 10, 2013

(54) SYSTEMS AND METHODS FOR STABILIZING A FUNCTIONAL SPINAL UNIT

(75) Inventor: Steven Seme, Savage, MN (US)

(73) Assignee: Centinel Spine, Inc., New York, NY (US)

( * ) Notice: Subject to any disclaimer, the term of this patent is extended or adjusted under 35 U.S.C. 154(b) by 1210 days.

(21) Appl. No.: 11/746,329

(22) Filed: May 9, 2007

(65) Prior Publication Data

US 2007/0265626 A1 Nov. 15, 2007

Related U.S. Application Data

(60) Provisional application No. 60/798,895, filed on May 9, 2006.

(51) Int. Cl.
*A61F 2/44* (2006.01)

(52) U.S. Cl.
USPC ........................................ 623/17.16; 606/249

(58) Field of Classification Search
USPC .................... 623/17.11–17.16; 606/248, 249
See application file for complete search history.

(56) References Cited

U.S. PATENT DOCUMENTS

| | | | | |
|---|---|---|---|---|
| 3,867,728 | A * | 2/1975 | Stubstad et al. | 623/17.16 |
| 5,674,296 | A | 10/1997 | Bryan et al. | |
| 6,093,205 | A | 7/2000 | McLeod et al. | |
| 6,440,169 | B1 * | 8/2002 | Elberg et al. | 623/17.16 |
| 6,540,785 | B1 | 4/2003 | Gill et al. | |
| 6,949,123 | B2 * | 9/2005 | Reiley | 623/17.11 |
| 7,611,537 | B2 * | 11/2009 | Carls et al. | 623/17.12 |
| 7,896,906 | B2 * | 3/2011 | Kwak et al. | 606/279 |
| 8,313,513 | B2 * | 11/2012 | Beger et al. | 606/249 |
| 2002/0123806 | A1 | 9/2002 | Reiley | |
| 2004/0006391 | A1 | 1/2004 | Reiley | |
| 2004/0049272 | A1 | 3/2004 | Reiley | |
| 2004/0049273 | A1 | 3/2004 | Reiley | |
| 2004/0049274 | A1 | 3/2004 | Reiley | |
| 2004/0049275 | A1 | 3/2004 | Reiley | |
| 2004/0049276 | A1 | 3/2004 | Reiley | |
| 2004/0049277 | A1 | 3/2004 | Reiley | |
| 2004/0049278 | A1 | 3/2004 | Reiley | |
| 2004/0049281 | A1 | 3/2004 | Reiley | |
| 2004/0111154 | A1 | 6/2004 | Reiley | |
| 2004/0143330 | A1 * | 7/2004 | Sazy | 623/17.11 |
| 2004/0210315 | A1 * | 10/2004 | Li et al. | 623/17.16 |
| 2004/0215341 | A1 * | 10/2004 | Sybert et al. | 623/13.17 |
| 2005/0027361 | A1 | 2/2005 | Reiley | |
| 2005/0043797 | A1 | 2/2005 | Lee | |

(Continued)

OTHER PUBLICATIONS

PCT Search Report mailed May 20, 2008; 7 pgs.

(Continued)

*Primary Examiner* — Jerry Cumberledge

(74) *Attorney, Agent, or Firm* — Tram Anh Nguyen; Donald D. Min

(57) ABSTRACT

Systems and methods for controlling motion and physiologic load sharing across a functional spinal unit defined by a pair of adjacent vertebrae and an intervertebral disc therebetween are provided. The systems may comprise a first component for repairing or replacing a disc nucleus, without substantially disrupting the annulus. A second component may be provided for attachment to the adjacent vertebrae, the second component being configured to control movement of the vertebrae relative to one another. The first and second components may be configured to cooperate simultaneously to control motion and collectively distribute physiologic load sharing across the functional spinal unit.

31 Claims, 12 Drawing Sheets

180
188a
184a
182
186a
186b
184b
188b

(56) References Cited

U.S. PATENT DOCUMENTS

| | | | | |
|---|---|---|---|---|
| 2005/0043799 | A1 | 2/2005 | Reiley | |
| 2005/0137705 | A1 | 6/2005 | Reiley | |
| 2005/0137706 | A1 | 6/2005 | Reiley | |
| 2005/0154467 | A1 | 7/2005 | Peterman et al. | |
| 2005/0171608 | A1 | 8/2005 | Peterman et al. | |
| 2005/0216081 | A1 | 9/2005 | Taylor | |
| 2005/0256578 | A1 | 11/2005 | Blatt et al. | |
| 2005/0277930 | A1 | 12/2005 | Parsons | |
| 2005/0277938 | A1 | 12/2005 | Parsons | |
| 2006/0009768 | A1* | 1/2006 | Ritland | 606/61 |
| 2006/0036240 | A1* | 2/2006 | Colleran et al. | 606/61 |
| 2006/0085074 | A1* | 4/2006 | Raiszadeh | 623/17.12 |
| 2006/0224159 | A1* | 10/2006 | Anderson | 606/61 |
| 2007/0106298 | A1* | 5/2007 | Carli et al. | 606/61 |
| 2007/0161992 | A1* | 7/2007 | Kwak et al. | 606/61 |
| 2007/0162001 | A1* | 7/2007 | Chin et al. | 606/61 |
| 2007/0173822 | A1 | 7/2007 | Bruneau et al. | |
| 2007/0233076 | A1* | 10/2007 | Trieu | 606/61 |
| 2007/0270838 | A1* | 11/2007 | Bruneau et al. | 606/61 |
| 2008/0114357 | A1* | 5/2008 | Allard et al. | 606/61 |
| 2010/0121379 | A1* | 5/2010 | Edmond | 606/249 |

OTHER PUBLICATIONS

K. Yong-Hing et al., "The Pathophysiology of Degenerative Disease of the Lumbar Spine," Symposium on Evaluation and Care of Lumbar Spine Problems, Orthopedic Clinics of North America, vol. 14, No. 3, Jul. 1983; pp. 491-504.

* cited by examiner

SYSTEMS AND METHODS FOR STABILIZING A FUNCTIONAL SPINAL UNIT

CROSS-REFERENCE TO RELATED APPLICATIONS

The subject matter of this application is related to the subject matter of U.S. Provisional Application Ser. No. 60/798,895, filed May 9, 2006 and entitled "Systems and Methods for Stabilizing a Functional Spinal Unit," priority to which is claimed under 35 U.S.C. §119(e) and an entirety of which is incorporated herein by reference.

FIELD OF THE INVENTION

The present invention relates to devices and methods for treating spinal conditions, and specifically to vertebral stabilization devices and methods of using such devices for stabilizing adjacent vertebrae. More specifically, the present invention relates to stabilization devices and systems for controlling motion and distributing physiologic load sharing across a functional spinal unit, and methods of using such devices and systems.

BACKGROUND OF THE INVENTION

The vertebral spine is the axis of the skeleton on which all of the body parts "hang." In humans, the normal spine has seven cervical, twelve thoracic, and five lumbar segments. The lumbar spine sits upon the sacrum, which then attaches to the pelvis, and in turn is supported by the hip and leg bones. The bony vertebrae of the spine are separated from one another by intervertebral discs which, as described below, act as a complex joint and provide a compressive load bearing structure.

With reference to FIG. 1, the typical vertebra 10 (such as the lumbar vertebra shown) has a thick anterior bone mass called the vertebral body 12. A vertebral or neural arch 14 is posteriorly defined relative to the vertebral body 12 via opposing pedicles 16. Laminae 18 are formed at the posterior side of the pedicles 16 and combine to form a spinous process 20. Thus, the spinous process 20 projects from the posterior region of the vertebral arch 14. In addition, transverse processes 22 project laterally from the respective pedicle 16/lamina 18 interface. Similarly, an opposing pair of superior articular processes 24 project upwardly from the respective pedicle 16/lamina 18 junction, each terminating in medially upward-facing facet 26. Conversely, two inferior articular processes 28 project downwardly from the respective pedicle 16/lamina 18 junction, and also terminate in a facet 30 (best shown in FIG. 2) that otherwise face laterally downward. As described below, the facets 26 or 30 interface with corresponding facets 26 or 30 of an adjacent vertebra to form part of a joint complex.

The center of adjacent vertebral bodies 12 are supported by an intervertebral disc 34. The intervertebral disc 34 primarily serves as a mechanical cushion permitting controlled motion within or between vertebral segments of the axial skeleton. The normal disc 34 is a unique, mixed structure, comprised of three component tissues: a nucleus pulposus ("nucleus") 36, an annulus fibrosus ("annulus") 38, and opposing vertebral end plates (not shown). The vertebral end plates are composed of thin cartilage overlying a thin layer of hard, cortical bone which attaches to the spongy, richly-vascular, cancellous bone of the corresponding vertebral body 12. The end plates thus serve to attach adjacent vertebral bodies 12 to the disc 34. The annulus 38 is a tough, outer fibrous ring consisting of 15 to 20 overlapping, multiple plies. Immersed within the annulus 38 is the nucleus 36. The healthy nucleus is largely a gel-like substance having a high water content, and like air in a tire, serves to keep the annulus 38 tight yet flexible. The nucleus 36 moves slightly within the annulus 38 when force is exerted on the adjacent vertebrae 10 while bending, lifting, etc.

With the above in mind, physiology of the spinal column is oftentimes described in terms of a functional spinal unit 50 as shown in FIG. 2. The functional spinal unit 50 consists of opposing, superior and inferior vertebrae 10*a*, 10*b*, and the intervening disc 34 that combine to generally define an anterior region or column 52 and a posterior region or column 54. The anterior region 52 consists of the opposing vertebral bodies 12*a*, 12*b* and the disc 34. Conversely, the posterior region 54 consists of the posterior portions of the vertebrae 10*a*, 10*b* (i.e., posterior of the respective vertebral bodies 12*a*, 12*b*), and the points of interface therebetween. In this regard, the inferior articular processes 28*a* (one of which is shown in FIG. 2) of the superior vertebra 10*a* engage with corresponding ones of the superior articular processes 24*b* (one of which is shown in FIG. 2) of the inferior vertebra 10*b*. The facets 30 (best shown for the inferior vertebra 10*b* in FIG. 2) of the superior vertebra's 10*a* inferior articular processes 28*a* nest or engage with a corresponding one of the facets 26 (FIG. 1) of the inferior vertebra's 10*b* superior articular processes 24*b*. When the adjacent vertebrae 10*a*, 10*b* are aligned, the corresponding, mated facets 26, 30 are encapsulated within cartilage and ligaments, forming an interlocking facet joint 56 (one of which is visible and referenced generally in FIG. 2). This is commonly referred to as a zygoapophyseal joint. In light of the vertebral anatomy, then, the posterior region 54 is characterized as including two of the facet joints 56 that, along with corresponding ligament structures (e.g., ligamentum flavum, intraspinous ligament, and supraspinous ligament), can collectively be referred to as the posterior joint complex. In addition, the disc 34 serves as a joint at the anterior region 52 such that the functional spinal unit 50 can be considered as establishing a three-joint complex including an anterior joint or anterior joint complex (i.e., the disc 34) and a posterior joint complex.

The physiological functions of these three joints are intimately linked. In general terms, the anterior joint complex 34 provides the primary compressive load bearing structure (i.e. axial compliance) and assists with rotational stability for the functional spinal unit 50, whereas the posterior joint complex provides primary motion (i.e., flexion, extension, and rotation) control. However, each joint of the three-joint complex affects these biomechanical functions. That is to say, the posterior joint complex 56 assists (or at least does not overtly impede) in supporting the functional spinal unit 50 when subjected to an axial or compressive load; similarly, the anterior joint complex 34 assists (or at least does not overtly impede) the posterior joint complex 56 in controlling motions of the functional spinal unit 50. Along these same lines, damage to one joint may lead or cascade to impairment of the opposing joint complex.

Painful, disabling degeneration of the functional spinal unit 50 can result from a number of different spinal pathologies that may increase in severity over time. In most instances, however, the initial degeneration of the functional spinal unit 50 is focused upon either the anterior region 52/anterior joint complex 34 or the posterior region 54/posterior joint complex 56. For example, disruption of the anterior joint, through disease or injury, can be attendant by a bulging or tearing of the annulus and/or nucleus degeneration. The resulting discal degeneration and/or loss of disc height can contribute to persistent and disabling back pain. Similarly, through disease or trauma, the ligamentous structures, laminae, spinous process, articular processes, and/or facets can become damaged (e.g., synovitas, subluxation of facet joints, osteophyte formation, etc.), resulting in an undesired anatomy, loss and/or change of mobility, and pain or discomfort.

In light of the above, treatment of a patient suffering from back pain or other spinal-related malady initially entails the physician identifying the location and form of primary degeneration (i.e., the anterior region 52/anterior joint complex 34 or posterior region 54/posterior joint complex 56). Once the joint pathology has been diagnosed, an appropriate treatment is selected. In some instances, the only viable treatment is complete fusion of both the anterior region 52 and the posterior region 54 of the functional spinal unit 50. Total (or 360°) fusion prevents any motion of the functional spinal unit 50 from occurring and thus is employed only in the most severe cases. More preferably, the selected treatment maintains or permits as much mobility of the functional spinal unit 50 as possible.

In recognition of the above, a plethora of non-fusion, motion preservation, prostheses, stabilization systems, etc., have been developed to correct degenerative pathology of either the anterior region 52/anterior joint complex 34 or the posterior region 54/posterior joint complex 56. For example, total disc replacement devices designed to replace the entire disc (nucleus and annulus) and restore motion are available from DePuy and Synthes Spine, to name but two. Also, prosthetic intervertebral disc nucleus devices by Raymedica, Disc Dynamics, and others focus upon replacing just the nucleus and mimic the columnar support provided by the natural disc. Conversely, various posterior joint repair systems and devices have been developed. For example, a variety of posterior stabilization technologies are available for controlling and/or restoring motion, such as spinal facet joint prosthesis from Archus Orthopedics, Inc. and Facet Solutions, Inc.; spinous process devices from Abbott Spine, Medtronic Sofamor Danek, and Paradigm Spine, LLC; and pedicular-based systems from Zimmer Spine and Applied Spine Technologies, Inc.; to name but a few.

It has surprisingly been discovered that while the various spinal treatment devices and methods may provide significant initial improvements to the particular joint complex being repaired, longer term implications on the opposing joint complex, and thus the functional spinal unit 50 as a whole, are not taken into consideration and thus are not addressed with the current technologies mentioned above. As a result, any "repair" directed toward one of the anterior or posterior joints may actually lead to or cause degeneration of the opposing joint complex due to the intimately linked nature of the functional spinal unit's entire three joint complex.

In light of the above, a substantial need exists for systems and methods for stabilizing a functional spinal unit in a manner facilitating proper biomechanical functioning in load sharing and motion control of the three-joint complex, as well as methods for selecting appropriate system components.

SUMMARY

The aforementioned needs, the present disclosure provides a system for controlling motion and physiologic load sharing across a functional spinal unit defined by a pair of adjacent vertebrae and an intervertebral disc therebetween. The system includes a first component and a second component. The first component is configured for repairing or replacing a disc nucleus without substantially disrupting the annulus, providing restoration of axial compliance. The second component is configured for attachment to the adjacent vertebrae, and provides primary control over movement of the vertebrae relative to one another. The first and second components of the system are configured to cooperate simultaneously to control motion and collectively distribute physiologic load sharing across the entire functional spinal unit.

A method of stabilizing a function spinal unit defined by a pair of adjacent vertebrae and an intervertebral disc therebetween is also provided by the present disclosure. The method includes providing a system for controlling motion and physiologic load sharing across the functional spinal unit, with the system including first and second components. The first component is adapted for repairing or replacing a disc nucleus, without substantially disrupting the annulus. The second component is provided for attachment to the adjacent vertebrae, and is configured to control movement of the vertebrae relative to one another. With this in mind, the first component is inserted into the disc nucleus space, and the second component is attached to the adjacent vertebrae. Upon final assembly, the first and second components of the system cooperate to simultaneously control motion and collectively distribute physiologic load sharing across the functional spinal unit.

Other aspects in accordance with principles of the present invention relate to a method of treating or stabilizing a degenerated functional spinal unit, where the functional spinal unit includes an intervertebral disc positioned between a superior vertebra and an inferior vertebra. The vertebrae combined define an anterior region and a posterior region, with the disc providing an anterior joint complex at the anterior region. In addition, the vertebrae form a posterior joint complex in the posterior region. With the above in mind, the method includes providing a functional spinal unit stabilization system including an anterior implant device and a posterior implant device. The anterior implant device is implanted in the anterior region, and is configured to mimic natural functioning of the anterior joint complex following implant (e.g., maintains motion and axial compliance). Similarly, the posterior implant device is implanted at the posterior region and is configured to mimic natural functioning of the posterior joint complex. Upon final implantation of the system, a majority of a columnar load placed upon the functional spinal unit is distributed to the anterior joint complex and is supported in part by the anterior implant device, while physiologic load sharing and motion control is maintained through the posterior implant device.

Yet another aspect in accordance with principles of the present invention relates to a method of making a functional spinal unit stabilization system for treating or stabilizing a functional spinal unit, where the functional spinal unit includes superior and inferior vertebrae, an intervertebral disc, and various ligamentous structures (e.g., ligamentum flavum, intraspinous and supraspinous ligaments, etc.). The functional spinal unit is characterized as defining an anterior region and a posterior region, with the disc providing an anterior joint complex and the vertebrae forming a posterior joint complex. With this in mind, the method may include evaluating a pathology of the functional spinal unit. An anterior implant device for implantation at the anterior region may be provided based upon the evaluation. More particularly, the anterior implant device may be adapted to support natural functioning of the anterior joint complex at a level implicated by the evaluation. Further, a posterior implant device for implantation at the posterior region may be provided based upon the evaluation. The posterior implant device may be adapted to support natural functioning of the posterior joint complex at a level dictated by the pathology evaluation. In this regard, the posterior implant device may be configured to provide minimal compressive support such that, upon final implantation, a majority of a columnar load placed upon the functional spinal unit is transversely distributed onto the anterior joint complex.

Still yet another aspect in accordance with principles of the present invention relates to a functional spinal unit stabilization system for treating a functional spinal unit. As described above, the functional spinal unit includes a superior vertebra, a disc, an inferior vertebra, and various ligamentous structures (e.g., ligamentum flavum, intraspinous and supraspinous ligaments, etc.), that combine to define an anterior region and a posterior region. The disc provides an anterior joint complex at the anterior region, whereas the vertebrae provide a posterior joint complex at the posterior region. The system may include an anterior implant device and a posterior implant device. The anterior implant device may be configured for implantation to the anterior region and is adapted to mimic normal functioning of the anterior joint complex. The posterior implant device may be configured for implantation to the posterior region and may be adapted to mimic normal functioning of the posterior joint complex. With this in mind, the anterior and posterior implant devices may be configured such that, upon final implantation, a majority of a columnar load placed upon the functional spinal unit is supported by the anterior implant device.

DETAILED DESCRIPTION OF THE INVENTION

The present invention generally relates to systems and methods for treating or stabilizing a functional spinal unit in a manner addressing and augmenting an entirety of a three-joint complex associated with the functional spinal unit, as well as methods for selecting components of the system. Functional spinal unit stabilization systems and methods of their use to control motion and physiologic load sharing across a functional spinal unit, defined by a pair of adjacent vertebrae and an intervertebral disc therebetween, are provided. The systems may comprise a first component for repairing or replacing a disc nucleus, without substantially disrupting the annulus. A second component may be provided for attachment to the adjacent vertebrae, the second component being configured to control movement of the vertebrae relative to one another. The first and second components of the systems are, in some embodiments, configured to cooperate simultaneously to control motion and collectively distribute physiologic load sharing across the functional spinal unit.

Figure 3:
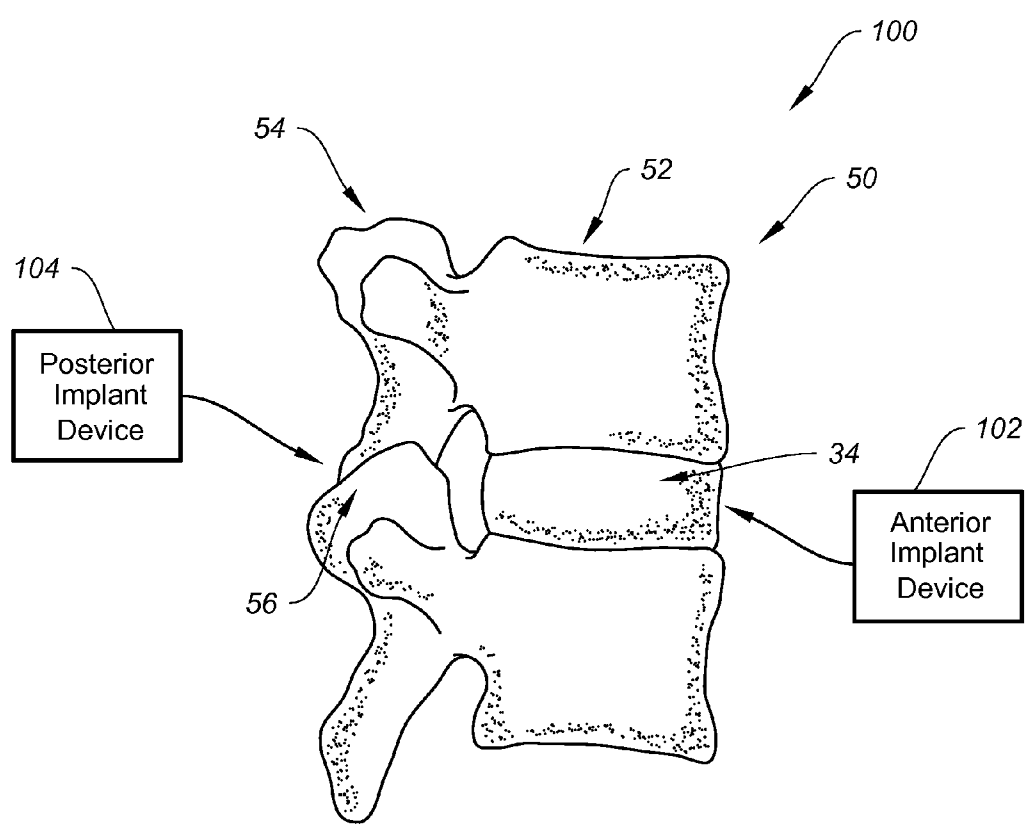
FIG. 3 illustrates in block form a functional spinal unit stabilization system in accordance with principles of the present invention along with a functional spinal unit.

FIG. 3 illustrates, in block form, a functional spinal unit stabilization system 100 in accordance with one aspect of the present invention, along with a functional spinal unit 50 as previously described. In general terms, the functional spinal unit stabilization system 100 may include a first component, or an anterior implant device 102, and a second component, or posterior implant device 104. As described in greater detail below, the first and second components, or anterior and posterior implant devices 102, 104, respectively, can assume a wide variety of forms. In more general terms, however, the anterior and posterior implant devices 102, 104 may be separately formed, yet configured in combination with one another and in light of the particular pathology presented by the functional spinal unit 50 to not only treat the patient's immediate pathology needs, but also to ensure restoration and/or maintenance of a load sharing balance across the functional spinal unit 50 and motion of the functional spinal unit 50.

As shown in FIG. 3, the anterior implant device 102 is, in some embodiments, configured for implantation to the anterior region 52 of the functional spinal unit 50. Conversely, the posterior implant device 104 is, in some embodiments, configured for implantation to the posterior region 54 of the functional spinal unit 50. Thus, the anterior implant device 102 can adapted to mimic and/or support the normal anterior joint complex 34 (referenced generally), whereas the posterior implant device 104 can be adapted to mimic or support normal functioning of the posterior joint complex 56 (referenced generally). In accordance with this description, in one embodiment, neither of the implant devices 102, 104 is a fusion device.

While the anterior and posterior implant devices 102, 104 can assume a variety of different forms in accordance with the present invention, certain constraints are specifically addressed in some embodiments. For example, the anterior implant device 102 can be configured to exhibit a resistance to compressive force while allowing disc height change and load sharing with the annulus 38, thus mimicking the natural anterior joint complex 34. In addition, the anterior implant device 102 can be configured to exhibit or otherwise allow for movement (e.g., flexion/extension, bending, and rotation) of the functional spinal unit 50 upon implantation. In other words, the anterior implant device 102 is configured, in accordance with some embodiments, to not overtly restrict or influence normal motion of the functional spinal unit 50. Conversely, the posterior implant device 104 is configured to restore, control and/or maintain motion of the functional spinal unit 50 in a manner mimicking that normally provided by a healthy, posterior joint complex. Thus, the anterior implant device 102 cannot assume a design configuration that otherwise might negatively impact functioning of the posterior joint complex 56 (e.g., the anterior implant device 102 cannot cause, when implanted, overloading of the facets 26, 28 otherwise forming the facet joints 56). The posterior implant device 104 can further be configured to exhibit a resistance to compressive force. However, a composition and/or size of the posterior implant device 104 cannot, following implant, cause an overt shift in force distribution of a columnar load from the anterior region 52 to the posterior region 54. That is to say, the posterior implant device 104 cannot control or dictate a height of the disc 34 independent of the anterior implant device 102, nor can it result in a columnar load sharing arrangement in which more than, for example 50%, of a columnar load is translated to, or supported by, the posterior region 54.

In light of the above constraints, the anterior and posterior implant devices 102, 104 may be configured in tandem, since a particular feature of one of the implant devices 102, 104 can affect a corresponding feature or component of the other implant device 102, 104. To this end, a resultant feature of this tandem design or selection process is to achieve, upon implantation, a biomechanical relationship within the functional spinal unit 50 whereby the anterior implant device 102 predominately or substantially controls displacement and maintenance of a height of the disc 34, whereas the posterior implant device 104 predominantly restores and/or controls motions thereby stabilizing the functional spinal unit 50. In this regard, the anterior and posterior implant devices 102, 104 may be configured such that, for example, 51-90%, of a columnar load placed upon the functional spinal unit 50 is translated to, or exerted upon, the anterior region 52 and 10-49% of the columnar load is translated to, or imparted upon, the posterior region 54. Thus, the anterior and posterior implant devices 102, 104 can be configured to accomplish any combination of load sharing within the ranges specified above that totals 100% and to address the particular pathology associated with the functional spinal unit 50.

Anterior Implant Device

Figure 4A:
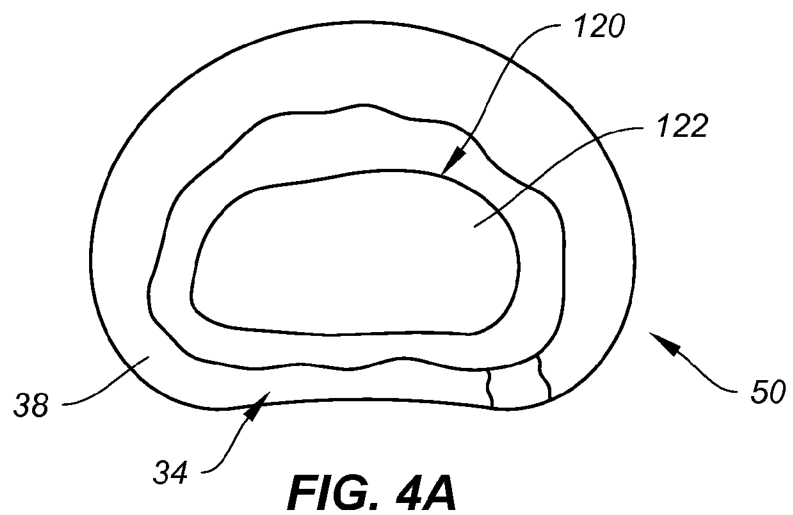
FIG. 4A is a superior view of an anterior implant device portion of the system of FIG. 3 in accordance with principles of the present invention and applied to an anterior region of a functional spinal unit.
Figure 4B:
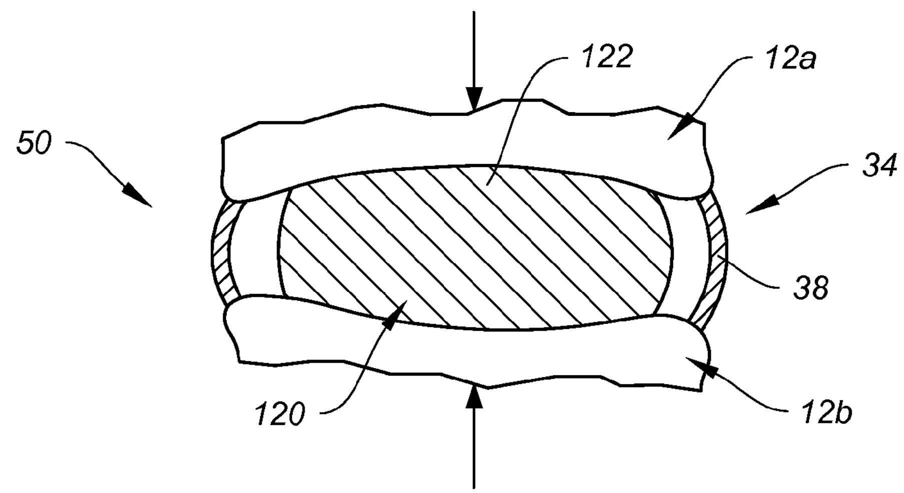
FIG. 4B is a sagittal cross-sectional view of the functional spinal unit/anterior implant device of FIG. 4A.

With the above general description in mind, one embodiment of a first component or anterior implant device 120 of the functional spinal unit stabilization system 100 is provided in FIGS. 4A and 4B in conjunction with relevant portions of the functional spinal unit 50 to which the anterior implant device 102 has been implanted. As a point of reference, the posterior implant device 104 (FIG. 3) and the posterior region 54 (FIG. 3) are not shown in the views of FIGS. 4A and 4B. In the one embodiment of FIGS. 4A and 4B, the device 102 comprises a nucleus replacement device 120 that is configured (e.g., in terms of size) to replace the natural nucleus 36 (FIG. 1) without significant disruption of the natural annulus 38. The nucleus replacement device 120 can assume a variety of forms, but generally consists of a core 122 that may or may not be externally and/or internally supported. More particularly, the core 122 may be a material or composition exhibiting viscoelastic properties, whereby the core 122 can deform while resisting compression (preferably providing increased resistance with increasing compressive loads), and consistently reverts to an original height following removal of the compressive load. By way of reference, arrows in FIG. 4B represent expected compressive loads experienced by the nucleus replacement device 120 when properly oriented upon implantation (it being understood that the compressive loads are into a plane of the drawing of FIG. 4A). For example, the core 122 can be a biocompatible, in situ curable polymer that is flowable in a first state for injection/insertion within the annulus 38. With subsequent curing, the polymer establishes a desired height of the disc 34, and deforms axially while resisting compressive loads normally experienced by the functional spinal unit 50 (e.g., weight of the patient when standing, when lifting small objects, etc.). For example, the core 122 can comprise or include a viscoelastic polymer such as polyurethanes, silicones, polycarbonate urethane, etc., that otherwise resist compression while providing minimal resistance to rotation of the anterior joint complex 34 (e.g., flexion/extension, lateral bending, and axial rotation).

Other polymers such as hydrogels (e.g., polymers with relatively high water content that resist shear forces and undergo shape change while absorbing water) can be utilized as the core 122. For example, the core 122 can be formulated/manufactured with a hydrophilic hydrogel such as polyacrylonitrile (e.g., acrylamide and acrylonitrile (block-polymer)). Alternatively, the hydrogel useful as the core 122 can be any hydrophilic acrylate derivative with a unique multi-block, copolymer structure or any other hydrogel material having the ability to deform and reform in a desired fashion in response to placement and removal of loads. For example, the hydrogel useful as the core 122 can be formulated as a mixture of polyvinyl alcohol and water. One such hydrogel is available under the trade name Hypan™ and is used in connection with a prosthetic spinal disc nucleus product available from Raymedica, LLC, of Bloomington, Minn., under the trade names PDN® and HydraFlex™. In fact, in some embodiments, the Raymedica PDN® or HydraFlex™ device can be used as the nucleus replacement device 120, although a wide variety of other device constructions are also acceptable.

Figure 5A:
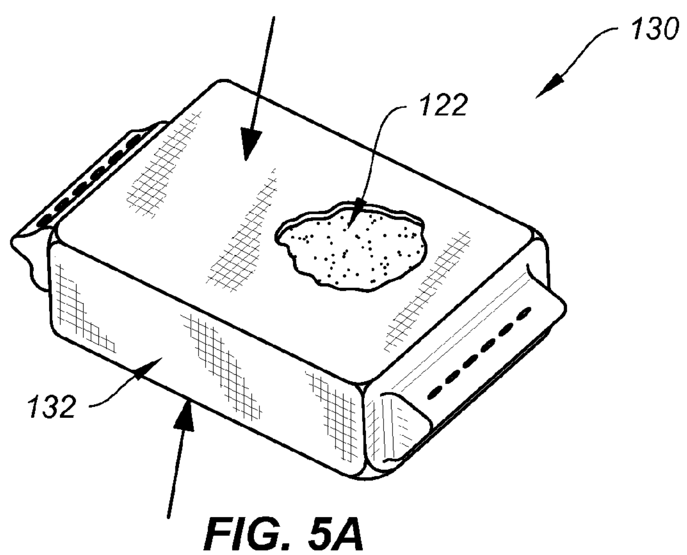
FIGS. 5A-5C illustrate alternative embodiment anterior implant devices in accordance with principles of the present invention.

As indicated above, the desired viscoelastic behavior and load support capabilities of the nucleus replacement device 120 can be augmented by the addition of an internal and/or external support structure or skeleton within the core 122 to provide increasing stiffness with increasing loads and improved creep resistance, while maintaining desired viscoelastic (spring-like) properties. For example, FIG. 5A illustrates in simplified form an alternative embodiment nucleus replacement device 130 useful as the anterior implant device 102 (FIG. 3). The nucleus replacement device 130 includes the core 122 described above and a support structure 132 in the form of an external skeleton surrounding the core 122. The support structure 132 can assume a variety of forms, and in one embodiment may be a woven, substantially inelastic (but deformable) jacket adapted to impart a prescribed stiffening effect to the core 122 at a desired core deformation in response to a compressive load (indicated by arrows in FIG. 5A). For example, the nucleus replacement device 130 can be a hydrogel-based, prosthetic spinal disc nucleus device as described in U.S. Pat. Nos. 5,674,295; 5,824,093; 6,132,465; and 6,602,291, the teachings of all of which are incorporated herein by reference. In general terms, the inelastic nature of the support structure 132 creates a directional stability within the nucleus replacement device 130, whereby increasing compressive loads are supported by the core 122 with minimal creep by limiting the amount the core 122 volumetrically can expand in length, width or any combination thereof. While the support structure 132 has been described as encompassing or surrounding an entirety of the core 122, in alternative embodiments, the support structure 132 can be open-ended (e.g., a ring or band surrounding a portion of the core 122). Similarly, the support structure 132 can be elastic (e.g., can have directional stretch properties) in other embodiments to further alter the load-deformation response properties of the device 120.

Figure 5B:
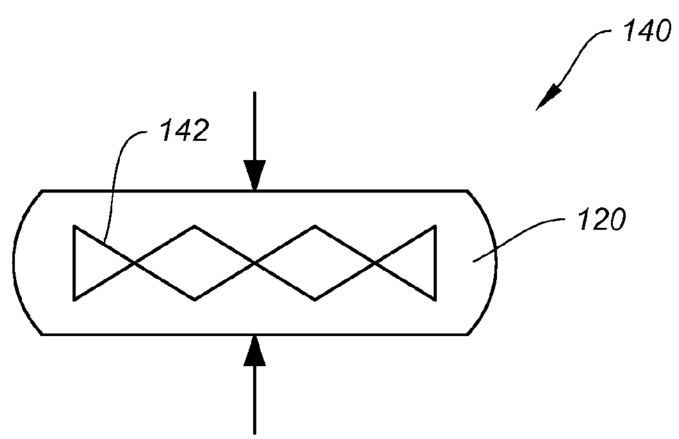

Another alternative embodiment anterior implant device 140 is shown in simplified form in FIG. 5B and may comprise the core 122 as previously described and an internal support structure 142 in the form of a frame disposed within the core 122. For example, the core 122 can be formed about the frame 142. Regardless, similar to the external support structure 132 described above, the frame 142 assists the core 122 in resisting and/or controlling device deformation in response to a compressive load (represented by arrows in FIG. 5B).

Figure 1:
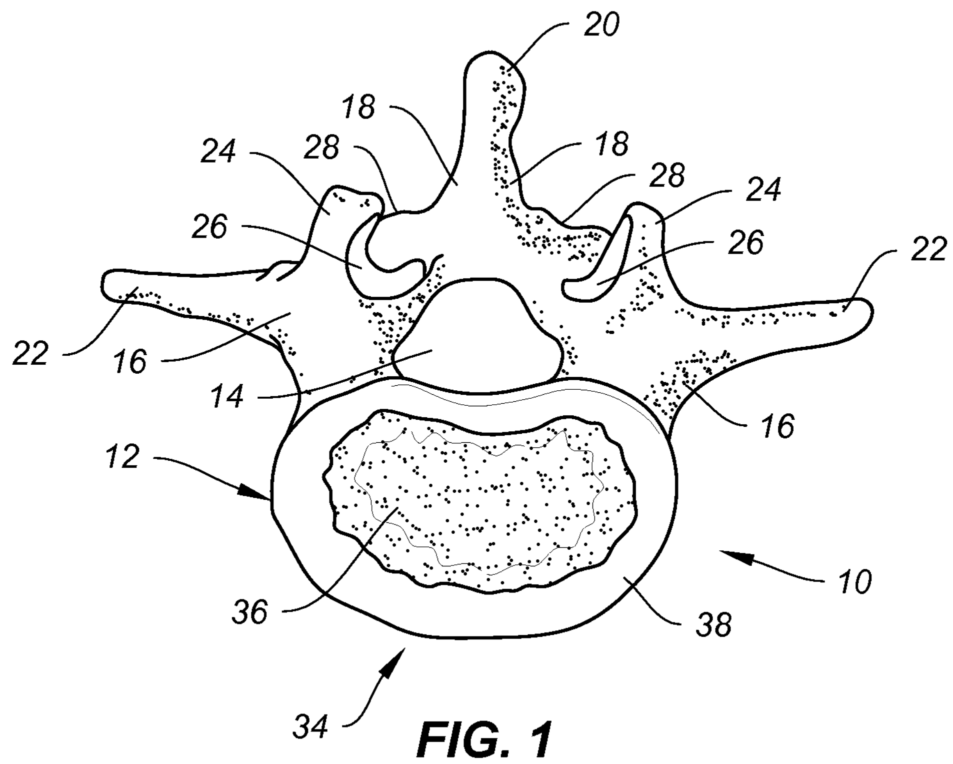
FIG. 1 is a superior view of a normal human lumbar vertebra and associated intervertebral disc.
Figure 5C:
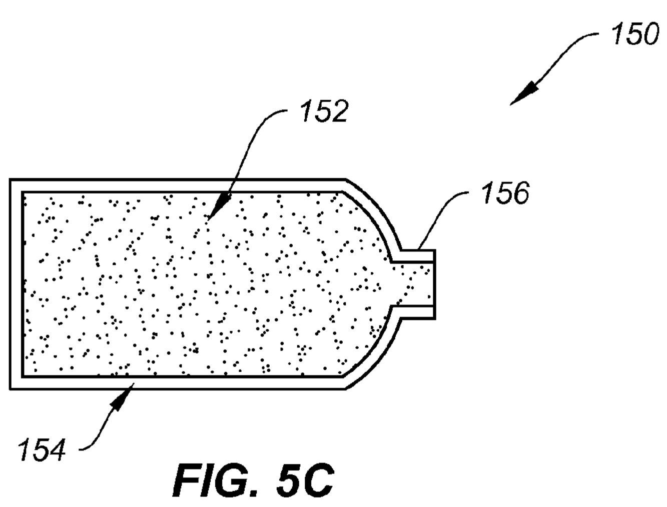

Yet another alternative embodiment anterior implant device 150 is shown in FIG. 5C and may comprise a core 152 and a support structure 154. The core 152 is akin to the core 122 previously described in that it may be a polymer or gel; however, unlike previous embodiments, the selected polymeric/gel material may be a viscous fluid and is thus less able to resist shear forces. The support structure 154 may be an inelastic (but deformable) or elastic skeleton or housing adapted to receive the core 152 in a flowable state, such as via an injection port/valve 156 as known in the art. With this configuration, the core 152 can be delivered within the support structure 154 in situ, following initial implantation of the support structure 154 within the annulus 38 (FIG. 1).

As should be evident from the foregoing, the anterior implant device 102 (FIG. 3) can assume any number of forms capable of deformably resisting compressive loads. To this end, while several embodiments have been described whereby the anterior implant device 102 can be a nucleus replacement device, in other embodiments, the anterior implant device 102 may be configured to replace the entire disc 34 (FIG. 1), including the annulus 38 (FIG. 1) and the nucleus 36 (FIG. 1). Regardless, a feature associated with some embodiments of the anterior implant device 102 of the present invention is an ability to simulate functioning of the anterior joint complex 34, allowing compression thereof while providing minimal resistance to natural motion of the anterior joint complex 34. The anterior implant device 102 should absorb energy, allow axial compression in a manner maintaining disc height (i.e., resist compression in a non-overt fashion), and allow relative vertebral body motion without causing an entirety of a columnar load to be directed solely upon the anterior region 52 in response to normal, expected columnar loads experienced by the functional spinal unit 50. In one embodiment, the selected anterior implant device 102 may exhibit a variable stiffness with increasing loads to better ensure the desired load balance.

Posterior Implant Device

As indicated above and with reference to FIG. 3, the second component of the functional spinal unit stabilization system 100, or the posterior implant device 104, may be configured in concert with the anterior implant device 102, as well as to address a particular pathology presented by the functional spinal unit 50 in question. In general terms, the posterior implant device 104 can primarily serve to restrict or control motion of the functional spinal unit 50, akin to a ligament, while not significantly altering the translation of columnar loads across the functional spinal unit 50. In other words, the posterior implant device 104 restores function and provides stabilization of the posterior joint complex 56, but does not, upon implant, produce or generate an overt shift in functional spinal unit columnar loads to the posterior region 54 by allowing at least some compression of the posterior region 54 to occur in the presence of columnar loads normally experienced by the functional spinal unit 50.

The above constraints give rise to a number of differing configurations for the posterior implant device 104 within the scope of the present disclosure. In some embodiments, the posterior implant device 104 is adapted to effectuate re-tensioning of the posterior ligamentous structure(s) (not shown) in a manner that may or may not be augmented with a tissue in-growth scaffold. More particularly, the posterior implant device 104 can be one or more components that augment (e.g., support or retains) the posterior ligamentous structure (s) following re-tensioning. For example, the supraspinous ligament of the patient is partially or fully removed from at least one spinous process. The ligament is then stretched and/or a section of the ligament is removed, followed by reattachment of the ligament to the spinous process with the posterior implant device 104 (e.g., clamp(s), staple(s), suture, scaffold, and/or anchor(s)), thereby creating a re-tensioning in the ligament while maintaining physiologic segment alignment. The re-tensioning stabilizes the spine segment in question, whereas the posterior implant device 104 augments strength until healing occurs. Further, segment motion stability is provided while promoting continued natural load transfer through the posterior joint complex 34. As a point of reference, the re-tensioned ligament provides the primary limit or control over motion of the posterior joint complex 34, such that in some embodiments, the posterior implant device 104 is more accurately characterized as the naturally occurring ligamentous structure(s) of the posterior joint complex 34, in contrast to a conventional implantable device. That is to say, in some embodiments, the system of the present disclosure consists of the anterior implant device 102 as described above in combination with re-tensioning of one or more ligaments of the posterior joint complex 34.

To augment the strength of the re-tensioned ligament during the healing process, the posterior implant device 104 can further include a structural member with tissue in-growth characteristics. For example, a scaffolding comprised of an appropriate material, such as Artelon® from Artimplant AB of Sweden, can be implanted in close proximity to the re-tensioned ligament. Alternatively, the scaffold can assume a variety of other tissue in-growth forms such as woven, braided, and/or embroidered materials.

In other, related embodiments, the supraspinous ligament is sectioned along its longitudinal length (cephaled-caudal) and the posterior implant device 104 is placed between the ligament sections, causing the ligament to move laterally (i.e., away from mid-line) to create the re-tensioning effect. Even further, an artificial and/or cadeveric ligament can be used as the posterior implant device 104, attached to the posterior vertebrae 10*a*, 10*b* in a partially stretched configuration. In yet other embodiments, the ligament re-tensioning techniques described above can be useful, standalone treatments, such that an anterior implant device is not required.

Figure 6C:
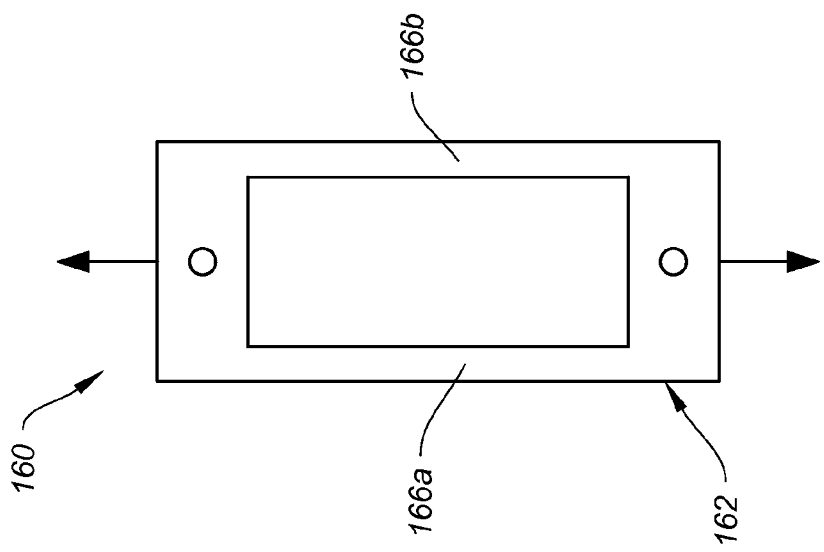
FIGS. 6A-6E illustrate a posterior implant device portion of the system of FIG. 3 in accordance with principles of the present invention.
Figure 6B:
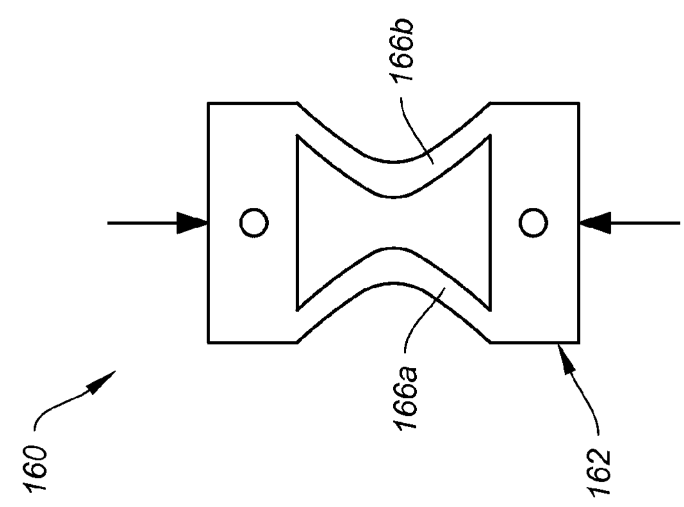
Figure 6A:
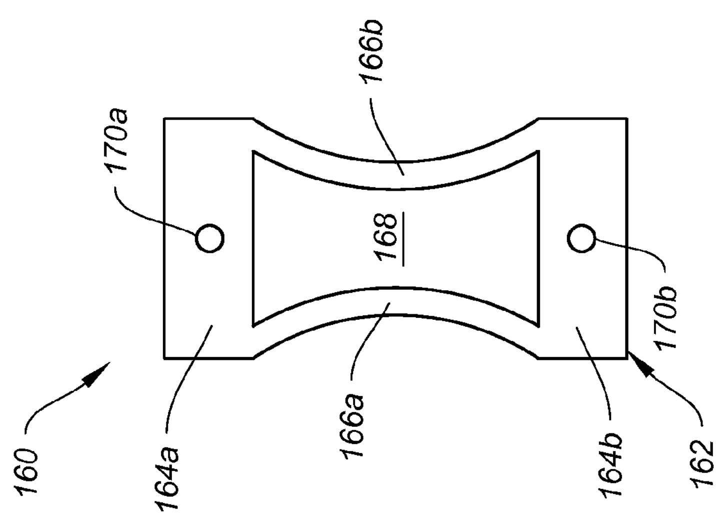

In other embodiments, the posterior implant device 104 can be in the form of a device that attaches to the bony anatomy to provide motion control. With this in mind, one possible embodiment of a posterior implant device 160 is shown in FIG. 6A. Posterior implant device 160 may include an implant body 162 defining opposing, first and second support members 164*a*, 164*b*, and opposing, first and second side members or struts 166*a*, 166*b*. In one embodiment, the implant body 162 may be integrally formed as a continuous structure from a non-linear elastic material (e.g., polymer), a superelastic material (e.g., shape memory alloy), an elastic material (metallic alloy), a composite of two or more of these materials, a polymer (e.g., PEEK), or polymer composite (e.g., fiber reinforced polymer). Alternatively, one or more of the support member(s) 164*a*, 164*b* and/or the side member(s) 166*a*, 166*b* can be separately formed and subsequently assembled. For example, the support members 164*a*, 164*b* and/or the struts 166*a*, 166*b* can be formed in a variety of fashions, such as solid, woven, braided, embroidered, etc. Even further, the support members 164*a*, 164*b* can have a first construction or material, and the struts 166*a*, 166*b* can have a different construction or material. Regardless, the support members 164*a*, 164*b* and the side members 166*a*, 166*b* may combine to define an aperture 168 that otherwise permits desired deflection of the side members 166*a*, 166*b* following implantation and during use as described below. As a point of reference, FIG. 6A illustrates the posterior implant device 160 in a natural state (i.e., not otherwise subjected to an external force or load).

Figure 2:
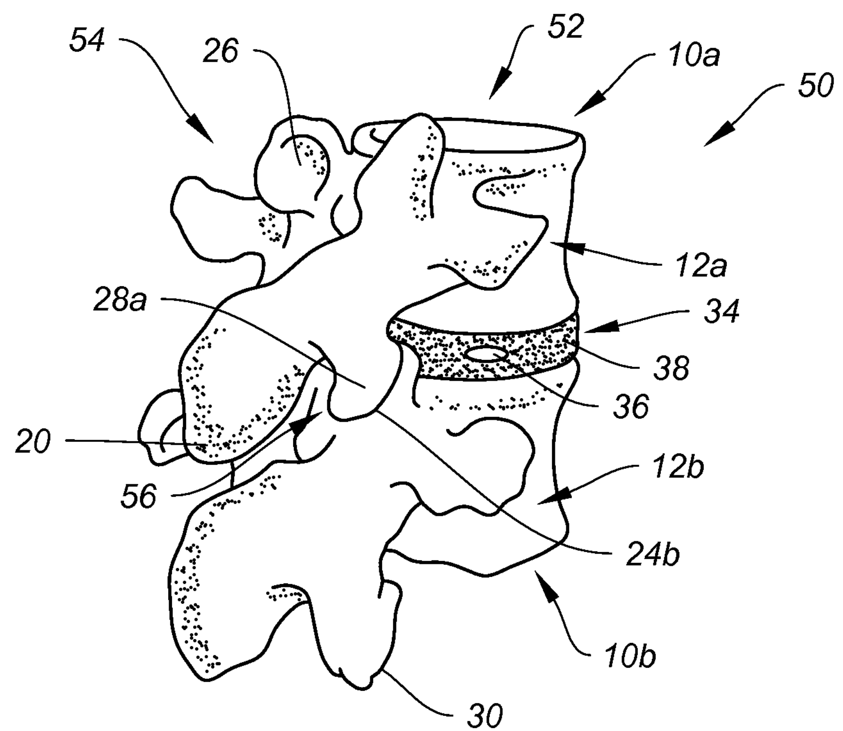
FIG. 2 is a posterior-lateral perspective view of a functional spinal unit including superior and inferior vertebrae and an intervertebral disc.

The support members 164*a*, 164*b* may be configured limit overt deflection of the side members 166*a*, 166*b*, as well as to facilitate attachment of the implant body 162 to the functional spinal unit 50 (FIG. 2). Along these lines, in one embodiment, each of the support members 164*a*, 164*b* forms an attachment feature 170*a*, 170*b* (drawn generally in FIG. 6A). The attachment feature 170*a*, 170*b* can assume a variety of forms, and in one embodiment is a hole that permits passage of an anchoring device (not shown), such as a screw, band, tube, tie, wire, bracket, etc., that is otherwise used to connect the corresponding support member 164*a*, 164*b* to a bony structure of the posterior region 54 (FIG. 2). For example, the anchoring device can be deployed to secure the corresponding support member 164*a*, 164*b* to the pedicle 16, laminae 18, spinous process 20 (FIG. 1), etc.

Regardless of how the support members 164*a*, 164*b* are configured and/or to what bodily site the support members 164*a*, 164*b* are anchored, the side members 166*a*, 166*b* may be configured to deflect from the unloaded state illustrated in FIG. 6A when the implant body 162 is subjected to various forces or loads (e.g., compressive, expansive, torsional, etc.). For example, and with reference to FIG. 6B, the side members 166*a*, 166*b* may deflect or buckle inwardly (reducing a size of the aperture 168) when the implant body 162 is subjected to a compressive force (represented by arrows in FIG. 6B), thereby reducing an overall height of the implant body 162. Thus, in the presence of a compressive load, the implant body 162 should not overtly resist compression of the posterior region 54 (FIG. 2) in a manner that might otherwise negatively affect desired, substantial focus of a columnar load at the anterior region 52 (FIG. 2). Conversely, when subjected to tension or expansive force (e.g., with forward flexion), the implant body 162, and in particular the side members 166*a*, 166*b*, can readily expand from the unloaded state of FIG. 6A, such that the implant body 162 increases in height as shown in FIG. 6C.

Figure 6D:
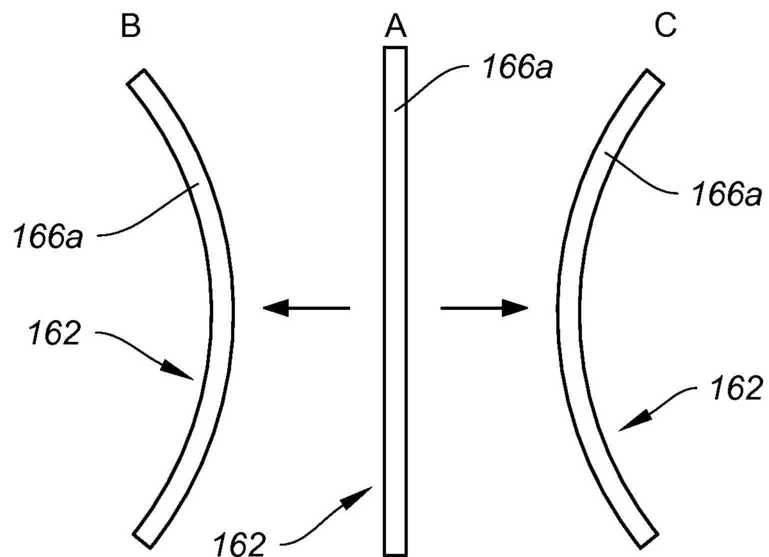

In addition to promoting desired columnar load sharing, the implant body 162 can be configured to control motion of the functional spinal unit 50 (FIG. 2) following implant. For example, and with reference to FIG. 6D, the side members 166*a*, 166*b* (it being understood that only the first side member 166*a* is visible in FIG. 6D) can deflect or "bow" posteriorly or anteriorly from an unloaded state ("A" in FIG. 6D). Thus, following implant, when the functional spinal unit 50 is subjected to a flexion moment force (e.g., the patient bends forward), the side members 166*a*, 166*b* not only expand from the natural state of FIG. 6A (i.e., as shown in FIG. 6C and described above), but also bow posteriorly ("B" in FIG. 6D) to a predetermined level so as to control the amount of permitted flexion. Similarly, when the functional spinal unit 50 is subjected to an extension moment force (e.g., the patient bends backwards), the side members 166*a*, 166*b* not only compress from the natural state of FIG. 6A (i.e., as shown in FIG. 6B and described above), but also bow anteriorly ("C" in FIG. 6D) to a predetermined level so as to control the amount of permitted extension.

Figure 6E:
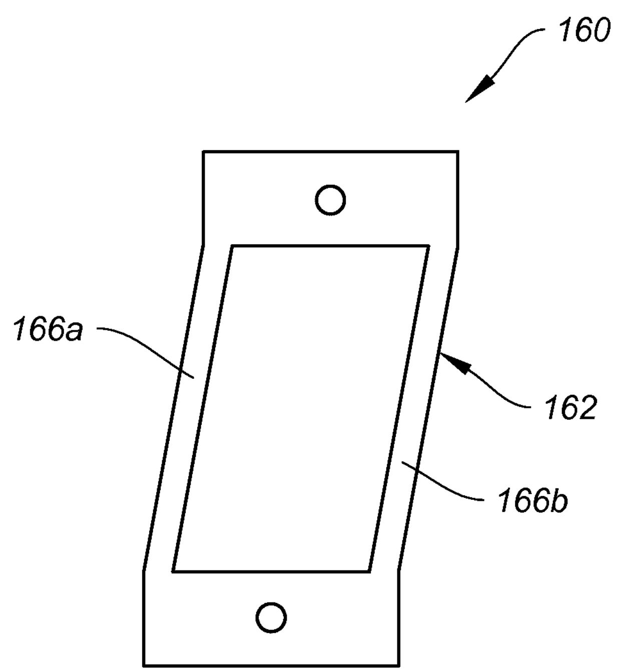

Finally, the implant body 162 may permit torsional movements in a controlled fashion. More particularly, the side members 166*a*, 166*b* may readily transition from the natural state of FIG. 6A to a torsionally deflected state (for example as shown in FIG. 6E) when subjected to a twisting motion (e.g., when, following implant, the patient rotates about the spinal axis). However, while the material(s) selected for the implant body 162 may impart a certain amount of "stretch" into the side members 166*a*, 166*b*, the amount of stretch/overall torsional movement is not unlimited; thus, the implant body 162 will resist/off-set increasing torsional moment forces.

Figure 7:
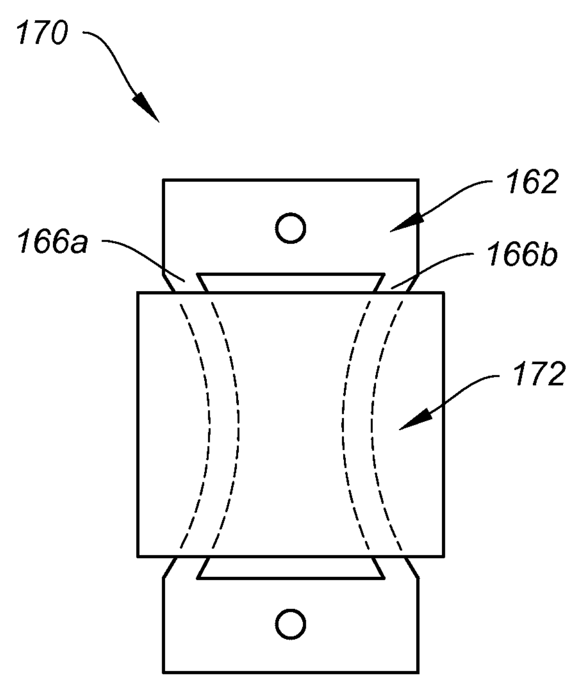
FIG. 7 is a rear plan view of an alternative embodiment posterior implant device in accordance with principles of the present invention.

The posterior implant device 160 can incorporate a number of additional design features and/or materials to generate desired properties that best "match" those presented by the anterior implant device 102 (FIG. 3). In particular, the posterior implant device 160 may be preferably configured to provide a desired stiffness (in terms of resistance to compression) that corresponds with a stiffness attribute of the anterior implant device 102, to ensure desired load sharing across the functional spinal unit 50 (FIG. 2) when subjected to a compressive columnar load. With this in mind, the additional components can be added to enhance the stiffness properties of the implant body 162. For example, FIG. 7 illustrates an alternative embodiment posterior implant device 170 that includes the implant body 162 previously described, along with a spacer 172 connected to the side members 166*a*, 166*b*. The spacer 172 can be a separately formed band that is attached to the side members 166*a*, 166*b*, a body formed (e.g., molded) about the side members 166*a*, 166*b*, etc. Regardless, the spacer 172 provides an incremental resistance to a compressive load placed upon the posterior implant device 170, as well as enhanced support of the side members 166*a*, 166*b* when subjected to flexion, extension and/or torsional forces.

Figures 8A, 8B:
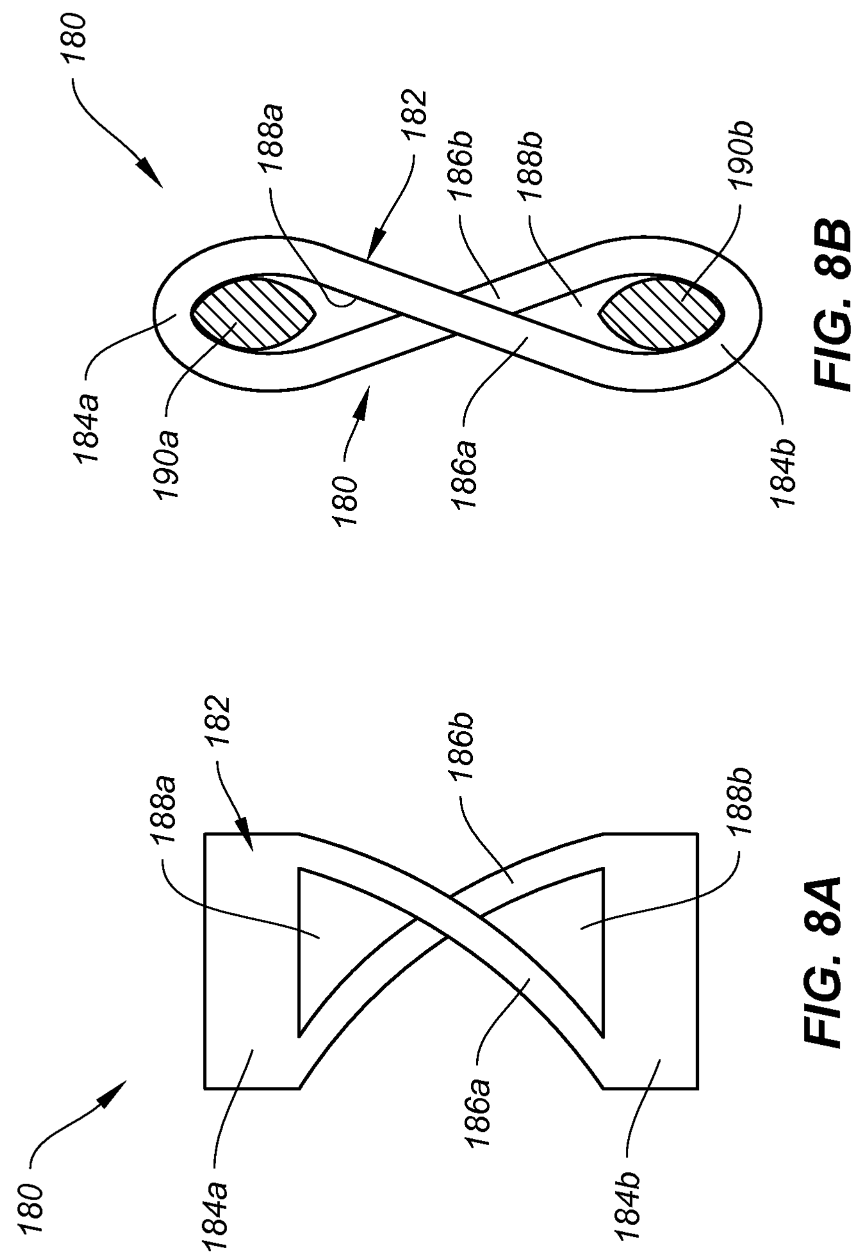
FIGS. 8A-8F illustrate alternative embodiment posterior implant devices in accordance with the present invention.

FIG. 8A illustrates another alternative embodiment posterior implant device 180 akin to the posterior implant device 160 (FIG. 6A) previously described, but with an enhanced torsional control. In particular, the posterior implant device 180 includes an implant body 182 similar to the implant body 162 (FIG. 6A) previously described in terms of material construction, and having opposing, first and second support members 184*a*, 184*b* and opposing, first and second side members or struts 186*a*, 186*b*. Unlike the implant body 162, the implant body 182 may be pre-fabricated or assembled/implanted in situ such that the side members 186*a*, 186*b* are twisted relative to one another. For example, in the embodiment of FIG. 8A, starting from an initial state akin to that shown in FIG. 6A, the first support member 184*a* is rotated relative to the second support member 184*b* such that the second side member 186*b* extends posteriorly across the first side member 186*a*, resulting in the arrangement shown in FIG. 8A. Alternatively, the first side member 186*a* can be positioned posterior the second side member 186*b*. Regardless, the resultant posterior implant device 180 provides a low level resistance to compression (as compared to the compression resistance attributed to the anterior implant device 102 (FIG. 3)), while exhibiting an enhanced resistance (as compared to the posterior implant device 160 of FIG. 6A) to flexion, extension and rotation/torsion.

The posterior implant device 180 can be configured for implant to the functional spinal unit 50 (FIG. 2) in a variety of manners. For example, the twisted arrangement of the side members 186*a*, 186*b* may generate opposing, first and second apertures 188*a*, 188*b*. As shown schematically in FIG. 8B, the apertures 188*a*, 188*b* may be conducive for placement over the spinous processes 190*a*, 190*b* (referenced generally) of the opposing vertebrae of the functional spinal unit 50 (not shown in FIG. 8B but illustrated in FIG. 2). The implant body 182 can be secured to the spinous processes 190*a*, 190*b* in any of the manners previously described (e.g., an anchoring device(s) that mounts the support member 184*a* or 184*b* to the corresponding spinous process 190*a* or 190*b*, etc.). The side members 186*a*, 186*b* may resist, to a certain extent, compressive forces, and provide a more overt resistance (as compared to the posterior implant device 160 of FIG. 6A) to flexion, extension and rotation/torsion.

Figure 8F:
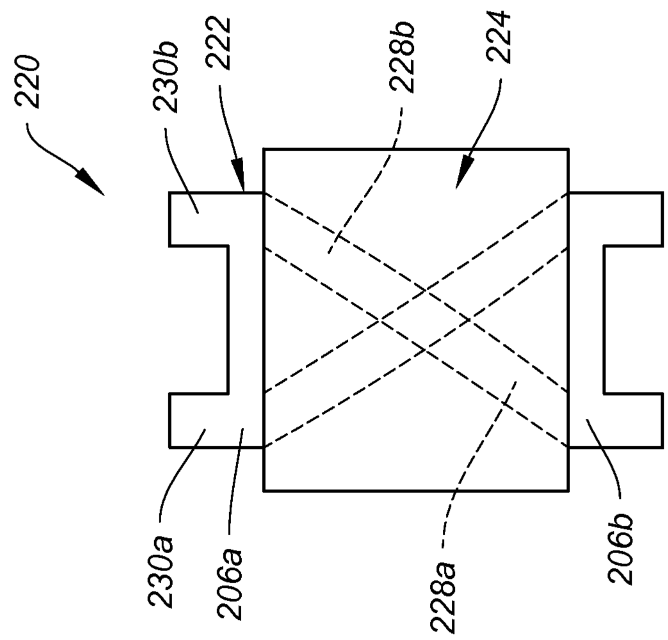
Figure 8C:
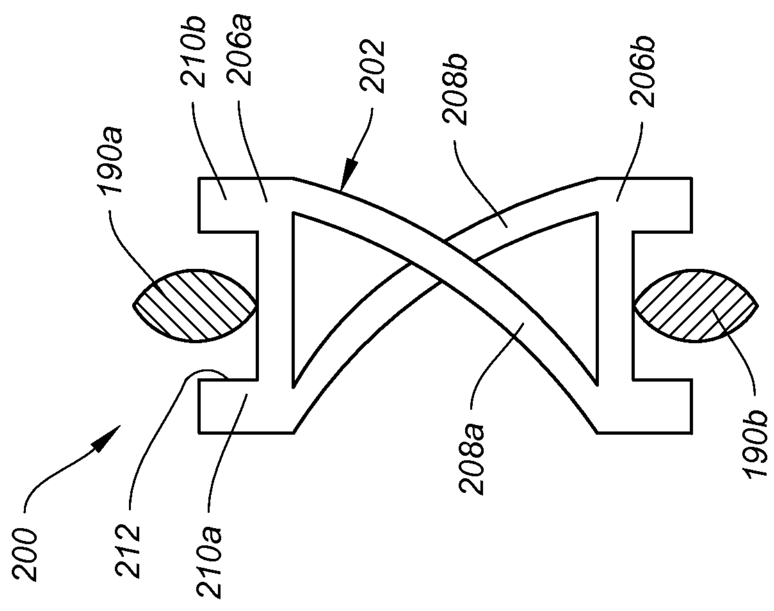
Figure 8D:
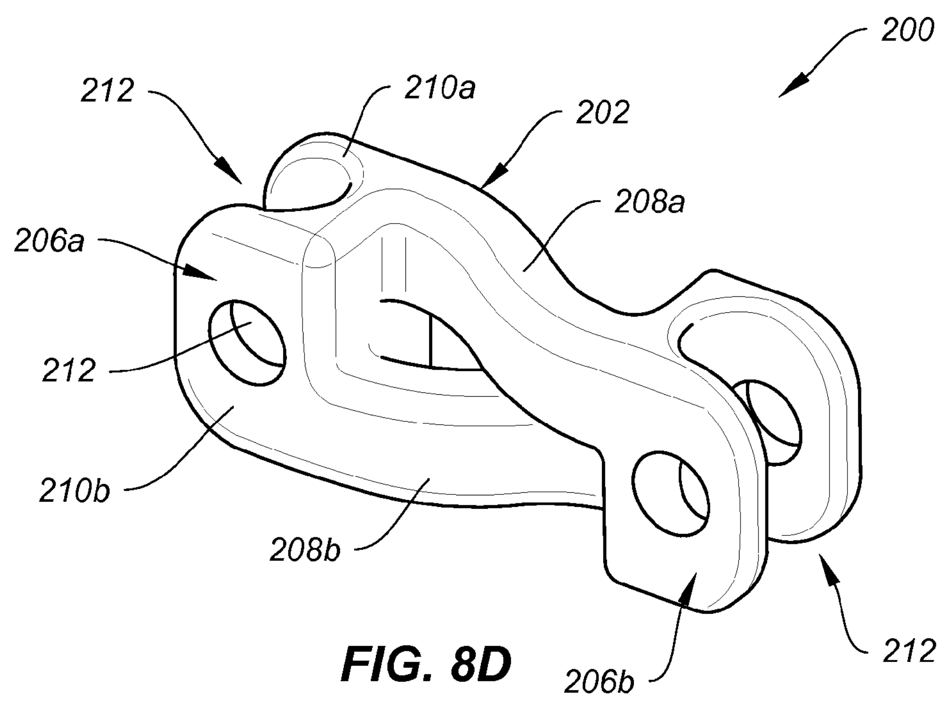
Figure 8E:
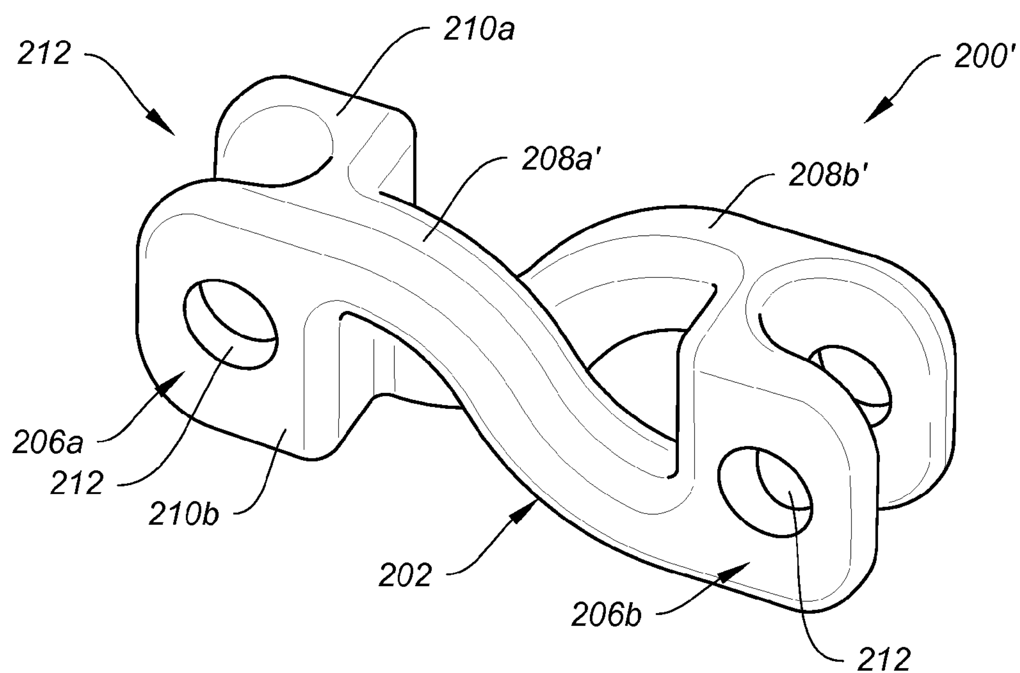

A related alternative embodiment posterior implant device 200 is illustrated in FIGS. 8C-8E. Posterior implant device 200 includes an implant body 202. The implant body 202 may be akin to the implant body 182 (FIG. 8A) previously described, and may include first and second support members 206*a*, 206*b*, and first and second side members 208*a*, 208*b*. In addition, the support members 206*a*, 206*b* may each include an opposing pair of arms 210*a*, 210*b* (identified for the first support member 206*a*) defining a slot 212 sized to receive a portion of the corresponding spinous process 190*a* or 190*b*. Once again, the support members 206*a*, 206*b*, including the corresponding arms 210*a*, 210*b*, can be mounted to the respective spinous process 190*a*, 190*b* in a variety of manners known in the art (screw, tube, wire, etc.). As shown in greater detail in FIG. 8D, the opposing pair of arms 210*a*, 210*b* further include or define through-holes 212, for placement of a fastener therethrough. Suitable fasteners may include, e.g., an anchoring devices that mount the support member 206*a* or 206*b* to the corresponding spinous process 190*a* or 190*b*, such as a bolt, fastener, screw, rivet, suture, ligament, or other tying device.

FIG. 8E illustrates a modification of the posterior implant device 200 of FIGS. 8C and 8D. As shown, the posterior implant device 200' includes all of the same structural elements as the devices 200 of FIGS. 8C and 8D, as evidenced by the same reference numerals to indicate like elements, except that the first and second side members 208*a'*, 208*b'* cross one another along a plane bisecting a longitudinal axis of the device 200'. In the embodiment of posterior implant device 200 shown in FIGS. 8C and 8D, the first and second side members 208*a*, 208*b* cross one another along a plane parallel to the longitudinal axis of the posterior implant device 200. Of course, it is understood that either twisting versions are suitable for use with the functional spinal unit stabilization system 100 (FIG. 2) of the present invention, so long as the side members (208*a* and 208*b* or 208*a'* and 208*b'*) overlap one another in such a manner as to generate an enhanced resistance to torsion/flexion/extension.

Yet another related alternative embodiment posterior implant device 220 is shown in FIG. 8F. The posterior implant device 220 includes an implant body 222 akin to the implant body 182 (FIG. 8A) or 202 (FIG. 8C) previously described, and a spacer 224. The implant body 222 further includes opposing, first and second support members 226*a*, 226*b* and opposing, first and second side members or struts 228*a*, 228*b*. In one embodiment, the support members 226*a*, 226*b* and the side members 228*a*, 228*b* may be integrally formed; alternatively, the members 226*a*-228*b* can be separately formed and subsequently assembled. Regardless, the support members 226*a*, 226*b* are configured for attachment to relevant bone(s) of the functional spinal unit 50 (FIG. 2), such as via arms 230*a*, 230*b* as previously described. In addition, the implant body 222 is configured such that the side members 228*a*, 228*b* overlap one another in a twisted fashion to generate an enhanced resistance to torsion/flexion/extension.

With the above in mind, the spacer 224 may be formed of a compressible material (e.g., a biocompatible foam) and is associated with the side members 228*a*, 228*b* to provide additional resistance to a compression force (shown by arrows in FIG. 8F) imparted upon the posterior implant device 220. For example, in one embodiment, the side members 228*a*, 228*b* can be embedded within the spacer 224 that otherwise extends from the first support member 226*a* to the second support member 226*b*. Alternatively, the spacer 224 can be disposed between the side members 228*a*, 228*b*. Regardless, the spacer 224 supports the side members 228*a*, 228*b* in the presence of compressive, expansion, and/or torsional forces.

The posterior implant device embodiments described above are but a few acceptable configurations in accordance with the present invention. Numerous other configurations can be provided via modification of know spinal facet joint prosthesis products. Pointedly, known spinal facet joint prosthesis products typically provide for at least one of flexion, extension and/or rotation, but are compressively rigid (in the presence of normally expected compressive loads) upon final implant. In this basic form, then, known spinal facet joint prostheses are likely unable to promote the load sharing balance provided by the present invention. Modification of such spinal facet joint prostheses thus entails incorporating a compression feature not otherwise present.

Such modification(s) constitute an improvement over known spinal facet joint prostheses designs. To this end, various other features associated with previous, current and future spinal facet joint prostheses can also be incorporated into the posterior implant device in accordance with the principles of the present invention. For example, but in no way limiting, frames, bearing surface(s), bone attachment mechanisms, adjustment features, etc., can further be included but are not specifically shown or described above. Along these same lines, existing or future spinal facet joint prostheses designs can be modified to include means for locating the device at various distances from the center of rotation of the functional spinal unit 50.

Methods of Stabilizing and Manufacturing

Returning to FIG. 3, the functional spinal unit stabilization system 100 in accordance with principles of the present invention can assume a wide variety of forms, as evidenced by the above discussion. While the anterior implant device 102 and the posterior implant device 104 can be provided apart from one another and can have entirely different constructions, the implant devices 102, 104 may also be formed or selected in tandem to both meet the needs of the particular functional spinal unit 50 pathology as well as to ensure desired, long-term compressive load balancing across the functional spinal unit 50, whereby a majority (e.g., greater than 51%) of a columnar compressive load experience by the functional spinal unit 50 may be directed to the anterior region 52 (and thus supported by the anterior implant device 102) with at least some of the compressive load (i.e., at least 10%) being transferred to the posterior region 54.

Commensurate with this general explanation, one embodiment of a method for stabilizing a functional spinal unit as well as configuring or selecting a functional spinal unit stabilization system in accordance with principles of the present invention may include performing an initial assessment of the patient's spinal health, including identifying the primary pathology/pathologies causing the patient's back-related pain. Any currently known and/or in the future devised technique for evaluating spinal health can be employed to analyze the patient's spine, including, for example, x-rays, MRI, discogram, etc. to name but a few. In instances where this evaluation reveals one or more unstable or abnormal functional spinal units, further evaluation may be done to diagnose the primary location and cause of functional spinal unit degeneration. Thus, as is known in the art, the physician can diagnose the patient for various spine-related deficiencies such as those caused by trauma or disease. To this end, the physician may ascertain whether the degeneration is primarily focused at the anterior region 52 (e.g., herniated or bulging disc, spondylolisthesis, etc.), the posterior region 54 (e.g., osteoarthritis, ankylosing spondylolysis, synovitis, etc.), or both.

In conjunction with the above diagnosis, the physician may evaluate the current health of the three joint complex associated with the functional spinal unit(s) 50 in question. Based upon this evaluation, the anterior implant device 102 and the posterior implant device 104 may be selected and/or configured in tandem to address both the immediate pathology present, as well as the overall stability of the functional spinal unit. For example, where it is determined that the posterior joint complex 56/posterior region 54 is degenerated, a more robust configuration of the posterior implant device 104 may be designed/selected for fully supporting or even replacing the posterior joint complex 56. That is to say, under this diagnosis scenario, the posterior implant device 104 may be akin to a spinal facet joint prosthesis. In addition to providing rigorous support/replacement of the posterior joint complex 56, the posterior implant device 104 may be selected/configured to include a degree of compressive flexibility (following implantation). This attribute may be selected/designed in accordance with a corresponding compression resistance attribute of the anterior implant device 102. Thus, and as previously described, the posterior implant device 104 may be selected/designed to allow for at least some compression of the functional spinal unit 50 to occur (i.e., will not prevent compression or otherwise serve to transfer all columnar loads on to the posterior region 54 following implant), but is also capable of providing some compression support.

In some embodiments, the iterative process of selecting/configuring the posterior implant device 104 under circumstances where the posterior region 54/posterior joint complex 56 is degenerated begins with a substantially known compressive stiffness characteristics of the anterior implant device 102. For example, the selection/design process may include first selecting a format for the anterior implant device 102 based upon a size/condition of the functional spinal unit 50. To this end, in one embodiment, the anterior implant device 102 may be a nucleus replacement device that, as described above, serves as a nucleus replacement and exhibits known deformation (or lack thereof) in the presence of compressive loads (i.e., has a known and repeatable compressive load vs. change in height curve). With this characteristic of the anterior implant device 102 in mind, the posterior implant device 104 can be further configured/selected to support/off-set the expected load transferred to the posterior region 54 following implantation. For example, it may be determined that the selected anterior implant device 102 will begin to deform (in height) when subjected to a compressive, columnar load in excess of X. Because columnar loads experienced by the functional spinal unit 50 of an adult may exceed X, the posterior implant device 104 may thus be configured/selected so as provide axial resistance to account for this situation (i.e., when the columnar load exceeds X.) Thus, the resultant system 100 is configured such that columnar load sharing occurs substantially through the anterior implant device 102 (e.g., in the range of 51%-90%), with the posterior implant device 104 providing only some compressive load support (e.g., in the range of 10%-49%). Conversely, the anterior implant device 102 may be configured/selected so as to not impede the posterior implant device 104 from controlling movement of the functional spinal unit 50 in the desired fashion (e.g., flexion, extension and/or rotation).

In other instances, it may be determined that the primary cause of the patient's back-related pain is degeneration of the anterior region 52/anterior complex joint 34. Under these circumstances, the anterior implant device 102 may be selected/designed to provide necessary columnar compressive support. In addition, the posterior implant device 104 is selected/designed with that some background or understanding in mind. Unlike the previous embodiment in which a posterior region 54 defect is addressed, under these circumstances, a less structurally rigorous design for the posterior implant device 104 can be employed (e.g., ligamentous retensioning). For example, the posterior implant device 104 need not include various features necessary to restore functioning of the entire posterior joint complex 34 (e.g., does not require invasive, facet reconstruction), as this level of repair is not indicated. However, recognizing that degeneration and/or subsequent repair of the anterior joint complex 34 may have a cascading effect on the posterior joint complex 56, the posterior implant device 104 in some form can be provided, and can be, for example, as basic as a suture or cord for interconnecting the opposing spinous processes of the vertebrae 10*a*, 10*b*, providing additional segment stability. Again, however, the selected/designed posterior implant device 104 should not have a configuration that might prevent any axial movement of the functional spinal unit 50 or otherwise cause a majority of a columnar load to be shifted to the posterior region 54.

Figure 9:
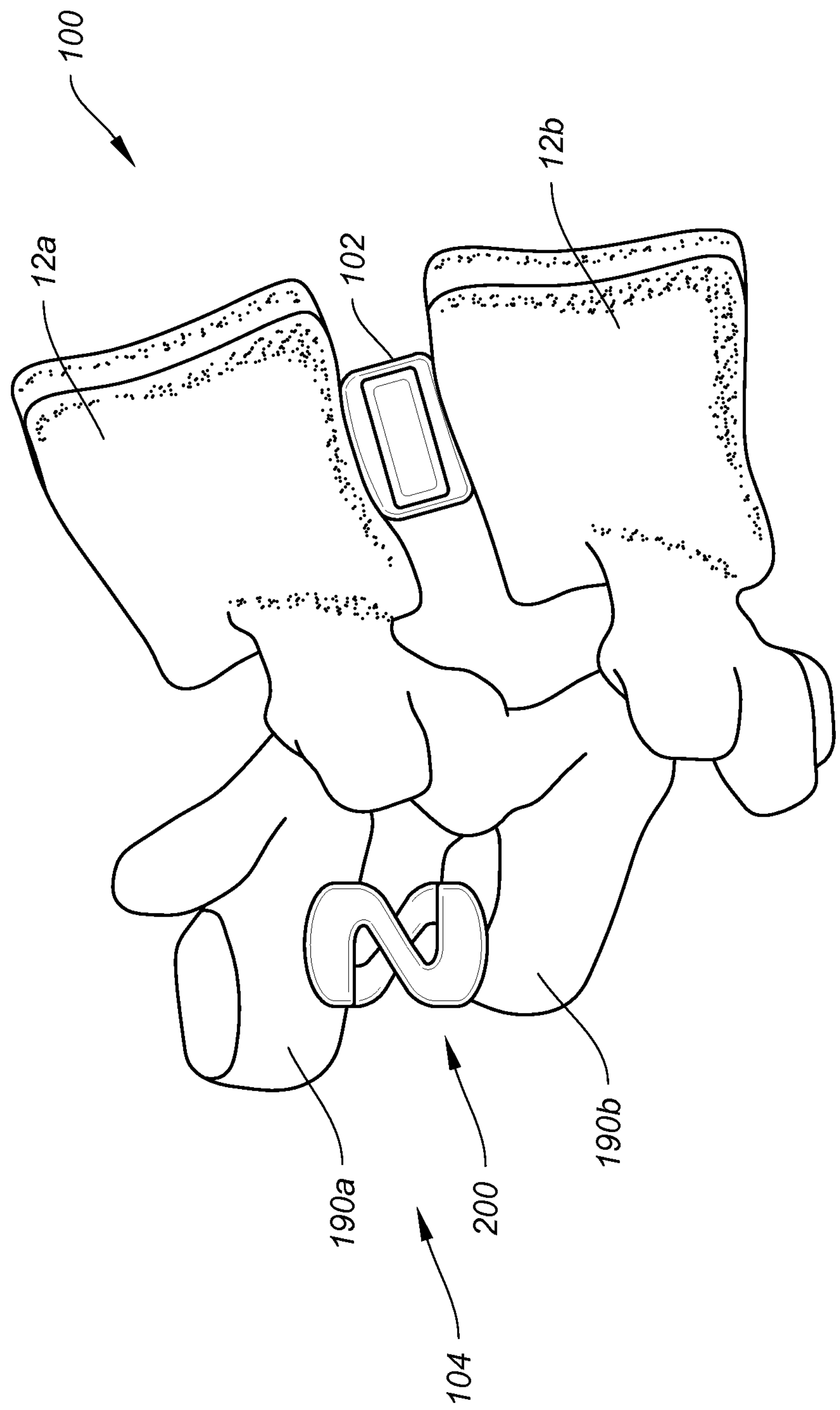
FIG. 9 illustrates a side view of a functional spinal unit stabilization system with an anterior implant device and the posterior implant device of FIG. 8D.
Figure 10:
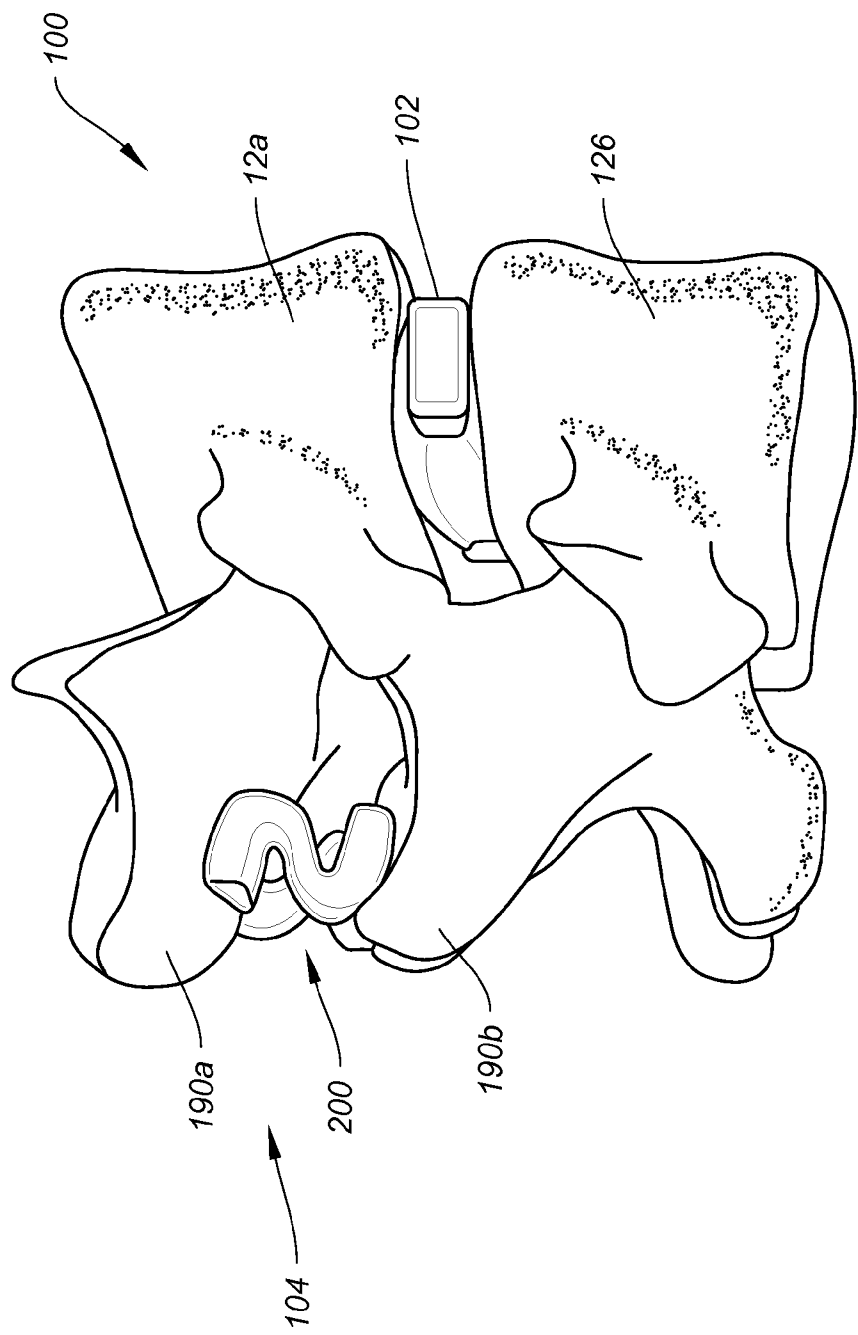
FIG. 10 illustrates a perspective view of the functional spinal unit stabilization system of FIG. 9.

Once the anterior implant device 102 and the posterior implant device 104 have been configured, selected or modified, the system 100 can implanted to the patient, as illustrated in FIGS. 9 and 10. As shown, the anterior implant device 102 may comprise a disc replacement device. The anterior implant device 102 can be implanted prior to the posterior implant device 104, or vice-versa. In this case, the posterior implant device 104 may comprise the posterior implant device 200, which has been secured to spinous processes 190*a*, 190*b*. Regardless, upon final implant, the three joint complex of the functional spinal unit 50 can be restored to near-normal health. Motion of the functional spinal unit 50 can controlled substantially through the posterior region 54, either by the posterior implant device 104 alone or by the natural posterior joint complex 56 with support from the posterior implant device 104. Columnar compressive loads experienced by the functional spinal unit 50 are shared or balanced across the anterior and posterior regions 52, 54, with a majority (51%-90%) of the compressive load being borne by the anterior region 52/anterior joint complex 34 (and thus the anterior implant device 102) and a minority (10%-49%) being supported or off-set at the posterior region 54. The posterior implant device 104 may or may not assist the natural posterior joint complex 56 in maintaining the integrity of the posterior region 54 in response to this compressive load.

The systems and methods of the present invention provide a marked improvement over previous designs. By addressing an entirety of the three joint complex of a functional spinal unit, the system and method overcomes the long-term problems inherent to conventional, non-fusion, spinal joint repair that focuses primarily on repair of only one joint complex.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A system for controlling motion and physiologic load sharing across a functional spinal unit defined by a pair of adjacent vertebrae, an anterior region and a posterior region, and an intervertebral disc having an annulus therebetween, the system comprising:

an anterior component, configured for implantation to the anterior region, for repairing or replacing a disc nucleus without substantially disrupting the annulus; and a posterior component for attachment to the adjacent vertebrae and being configured to control movement of the vertebrae relative to one another, the posterior component comprising support members and strut members, wherein each strut member is twisted relative to the other such that the posterior component has a twisted configuration for enhanced resistance to torsion, flexion or extension;

wherein the anterior component and posterior component are configured to cooperate simultaneously to control motion and collectively distribute physiologic load sharing across the functional spinal unit.

2. The system of claim 1, wherein the anterior component is configured to resist compressive loads without significantly altering a natural motion of the functional spinal unit.

3. The system of claim 1, wherein the posterior component is configured to limit motion of a posterior joint complex of the functional spinal unit without significantly altering a natural compressive load transfer through the anterior joint complex.

4. The system of claim 1, wherein the anterior component comprises a viscoelastic polymer.

5. The system of claim 4, wherein the polymer is selected from the group consisting of hydrogel, polyurethane, silicone, and polycarbonate urethane.

6. The system of claim 5, wherein the polymer comprises an injectable material.

7. The system of claim 6, wherein the injectable material comprises a curable polymer.

8. The system of claim 4, further including an envelope at least partially surrounding the polymer for constraining and structurally supporting the viscoelastic polymer.

9. The system of claim 8, wherein the envelope includes an injection port for introduction of the polymer.

10. The system of claim 8, wherein the envelope is inelastic but deformable.

11. The system of claim 8, wherein the envelope is at least partially elastic.

12. The system of claim 8, wherein the envelope comprises a woven jacket.

13. The system of claim 4, further including an internal scaffold constraining and for structurally supporting the viscoelastic polymer.

14. The system of claim 13, wherein the internal scaffold is inelastic but deformable.

15. The system of claim 13, wherein the internal scaffold is at least partially elastic.

16. The system of claim 15, wherein the internal scaffold comprises a spring-like element.

17. The system of claim 1, wherein the posterior component is configured to attached to a pedicle of at least one of the adjacent vertebrae.

18. The system of claim 1, wherein the posterior component is configured to attach to a laminar surface of at least one of the adjacent vertebrae.

19. The system of claim 1, wherein the posterior component is configured to attached to a spinous process of at least one of the adjacent vertebrae.

20. The system of claim 19, wherein the posterior component comprises an interspinous stabilization device configured for attachment to the spinous processes of the adjacent vertebrae.

21. The system of claim 20, wherein the interspinous stabilization device comprises a pair of spinous process attachment portions, and at least one strut extending therebetween.

22. The system of claim 21, wherein the least one strut is comprised of a semi-elastic biocompatible material selected from the group consisting of naturally occurring materials and synthetic materials.

23. The system of claim 22, wherein the at least one strut is resiliently deformable.

24. The system of claim 23, further comprising two resiliently deformable struts.

25. The system of claim 24, wherein the two resiliently deformable struts cross one another.

26. The system of claim 21, wherein the at least one strut comprises a multiple layer composite.

27. The system of claim 26, wherein each layer of the multiple layer composite comprises a different material.

28. The system of claim 20, wherein the interspinous stabilization device is configured to resist torsion.

29. The system of claim 20, wherein the interspinous stabilization device has a preload in compression.

30. The system of claim 1, wherein the posterior component is configured to be attached at a distance away from a center of rotation of the functional spinal unit.

31. A functional spinal unit stabilization system for treating a functional spinal unit including superior and inferior vertebrae and an intervening intervertebral disc, the functional spinal unit defining an anterior region and a posterior region, wherein the disc provides an anterior joint complex and the vertebrae provide a posterior joint complex, the system comprising:

an anterior implant device configured for implantation to the anterior region and adapted to mimic normal functioning of the anterior joint complex; and a posterior implant device configured for implantation to the posterior region and adapted to mimic normal functioning of the posterior joint complex, the posterior implant device comprising support members and strut members, wherein each strut member is twisted relative to the other such that the posterior device has a twisted configuration for enhanced resistance to torsion, flexion or extension;

wherein the anterior and posterior implant devices are configured such that upon implantation, a majority of a columnar load placed upon the functional spinal unit is supported by the anterior implant device.

* * * * *